United States Patent
Terasaki et al.

(10) Patent No.: US 6,276,536 B1
(45) Date of Patent: Aug. 21, 2001

(54) METHOD OF MEASURING RIPENESS AND TEXTURE OF VEGETABLE OR FRUIT AND MEASURING INSTRUMENT

(75) Inventors: Shoji Terasaki; Naoki Wada, both of Ehime (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/424,639
(22) PCT Filed: Mar. 30, 1999
(86) PCT No.: PCT/JP99/01609
§ 371 Date: Mar. 3, 2000
§ 102(e) Date: Mar. 3, 2000
(87) PCT Pub. No.: WO99/50653
PCT Pub. Date: Oct. 7, 1999

(30) Foreign Application Priority Data

Mar. 31, 1998 (JP) ................................. 10-085707
Sep. 29, 1998 (JP) ................................. 10-274937

(51) Int. Cl.[7] ........................................ B07C 5/34
(52) U.S. Cl. .................. 209/599; 209/556; 209/592; 209/590; 73/579; 73/653; 73/657; 73/659; 702/194; 702/56; 702/75; 702/76; 702/77
(58) Field of Search .................. 209/599, 556, 209/592, 590; 73/579, 655, 657, 659; 702/56, 75, 76, 77, 194

(56) References Cited

U.S. PATENT DOCUMENTS 5,152,401   10/1992   Affeldt, Jr. et al. .

FOREIGN PATENT DOCUMENTS 10-73572   3/1998   (JP) .

OTHER PUBLICATIONS

"Automatic Recording of Vibrational Properties of Foodstuffs", Birger Drake, Swedish Institute for food Preservation Research, Gotchorg, Sweden, May 10, 1961, pp 182–88.

*Primary Examiner*—Donald P. Walsh
*Assistant Examiner*—Jonathan R. Miller
(74) *Attorney, Agent, or Firm*—Wenderoth, Lind & Ponack, L.L.P.

(57) ABSTRACT

A method for measuring the ripeness and the texture of a fruit, the method comprising a step for applying a vibration having sequentially hanging frequencies to a fruit to be measured, a step for measuring the intensity of the vibration applied to the fruit and the intensity of the vibration of the fruit, a step for measuring the weight of the fruit, a step for finding the transfer functional characteristic of the fruit by performing frequency analysis based on the intensity of the vibration applied to the fruit and the intensity of the vibration of the fruit, and computing the secondary resonance frequency $f_0$ (i.e., frequency of secondary resonance peak) of the fruit and the frequencies f1 and f2 which represent the resonance frequencies of the fruit, at which respective gains are 3 dB lower than the gain at the frequency $f_0$ of the secondary resonance peak, based on the transfer functional characteristic of the fruit, a step for computing the damping ratio η and the elasticity value E of the fruit based on the weight of the fruit and the frequencies $f_0$, f1 and f2, a step for determining the ripeness of the fruit by using the elasticity value E when the elasticity value E is larger than a predetermined value, and by using the damping ratio η when the elasticity value E is not larger than the predetermined value, a step for computing the viscosity value c and the elasticity value E of the fruit based on the weight of the fruit and the frequencies $f_0$, f1 and f2, and a step for determining the texture and the ripeness of the fruit from the relation between the viscosity value c and the elasticity value E. The above method enables timely shipment of fruits to the market.

11 Claims, 8 Drawing Sheets

Shift of secondary resonance peak by ripening in kiwi fruit

Shift of secondary resonance peak by ripening in kiwi fruit

Transfer functional characteristic
having secondary resonance peak
from which damping ratio is computed Relation between damping ratio η and elasticity value E in kiwi fruits of various ripeness Process of ripeness judgment performed by microprocessor (in kiwi fruit)

METHOD OF MEASURING RIPENESS AND TEXTURE OF VEGETABLE OR FRUIT AND MEASURING INSTRUMENT

FIELD OF THE INVENTION

The present invention relates to a method and an apparatus for measuring the ripeness and the physical characteristics (hereinafter referred to as texture) such as hardness, resistance to teeth and glutinousness of fruits such as a kiwifruit, an apple, a melon, a tomato and the like, and vegetables, without damaging the fruits to be measured. More particularly, the present invention relates to a technology for finding the ripeness and the texture of a fruit from the relation between the elasticity value and the damping ratio, and, from the relation between the viscosity value and the elasticity value of the fruit.

BACKGROUND OF THE INVENTION

For measuring the ripeness of a fruit without damaging the fruit, a method of measuring the change of the color of the fruit and a method of measuring the hardness of the surface of the fruit are tried. However, the former can not be applied for a kiwifruit, a pear and the like whose color does not change in the process of ripening, and, in the latter, there is big discrepancy between the measured result and the actual ripeness of the fruit because the hardness of the surface of the fruit does not represent the hardness of the flesh of the fruit.

Also, a method for measuring the sugar content of a fruit by using the technology of the spectral diffraction of near infrared rays is launched for practical use in sorting fruits such as melons, peaches and the like by ripeness. However, in this method, a just ripe fruit and a rotten fruit can not be discriminated because both have similarly high content of sugar, though the sugar content increases in the process of changing from unripe to ripe.

In the quality of a fruit, texture is an important factor as well as taste. In the United States, the judgment of the texture of an apple is performed by the panel test of experienced judging members. However, in this method, an objective judgment of the texture is hardly obtained because the judgments of the respective members are subject to the respective experiences and the likes of the members.

In plant physiology, it is known that the texture, i.e., the physical characteristics such as hardness, resistance to teeth, glutinousness and the like of a fruit relate to the viscosity value and the elasticity value of the fruit.

The softening of a fruit is caused by the change of the characteristics of the viscosity and the elasticity of the cell wall of the fruit. The mechanical structure of the cell wall of a fruit is maintained in such a manner that bundles of crystalline cellulose surrounded respectively by highly polymerized polysaccharides (i.e. matrix gel) are united by winding each other. The softening of a fruit is caused by the loosening of the winding of the bundles of the crystalline cellulose, which is caused by the low polymerization of the matrix gel. The polysaccharides which compose the matrix gel comprise various substances, and the substance which is low polymerized in the softening is different depending on the kind of fruit. As a result, the state of the matrix gel of a ripe fruit is different depending on the kind of fruit. The rough taste in the flesh of an apple or the like and the thick taste in the flesh of a berry such as kiwifruit or the like are caused by the different state of the matrix gel of each. The state of the matrix gel of a fruit represents the glutinousness of the fruit. In other words, the viscosity value of a fruit represents the feeling in eating such as the glutinousness, juiciness and the like of the fruit. Also the elasticity value of a fruit represents the elasticity force of the cell wall of the fruit, i.e. the hardness of the flesh of the fruit.

B. Drake designed a viscosity measuring apparatus for objectively measuring the texture of foodstuffs such as fruits by utilizing the fact that the texture can be shown by the characteristics of the viscosity and the elasticity of the foodstuffs (J. Food Sci. 27. P182–188:1962). The method is to compute the damping ratio $\eta$ of the foodstuff to be measured by an equation $\eta=\Delta f/f_0$, in which $f_0$ is the intrinsic resonance frequency of the foodstuff, which is obtained by measuring the rectangular slice of the foodstuff, on which a vibration is applied, and $\Delta f$ is a half-power bandwidth. And the damping ratio $\eta$ thus computed is deemed as the viscosity value of the foodstuff.

However, in this method also, the foodstuff to be measured is damaged because the rectangular slice has to be taken from the foodstuff for the measurement.

SUMMARY OF THE INVENTION

A method for measuring the ripeness and the texture of a fruit in the present invention, for addressing the above conventional problems, comprises a step for applying a vibration having sequentially changing frequencies to a fruit to be measured, a step for measuring the intensity of the vibration applied to the fruit and the intensity of the vibration of the fruit, a step for measuring the weight of the fruit, a step for finding the transfer functional characteristic of the fruit by performing frequency analysis based on the intensity of the vibration applied to the fruit and the intensity of the vibration of the fruit, and computing the secondary resonance frequency $f_0$ (i.e., frequency of secondary resonance peak) of the fruit and the frequencies f2 and f1 which represent the frequencies of the fruit, at which respective gains are 3 dB lower than the gain at the frequency $f_0$ of the secondary resonance peak, a step for computing the damping ratio $\eta$ defined by an equation $\eta=(f2-f1)/f_0$ and the elasticity value E defined by an equation $E=m^{2/3}\cdot f_0^2$, of the fruit, in which m represents the weight of the fruit, a step for determining the ripeness of the fruit by using the elasticity value E when the elasticity value E is larger than a predetermined value and by using the damping ratio $\eta$ when the elasticity value E is not larger than the predetermined value, a step for computing the damping ratio $\eta$ defined by the equation $\eta=(f2-f1)/f_0$, the viscosity value c defined by an equation $c=k\cdot f_0\cdot m\cdot\eta$ and the elasticity value E defined by the equation $E=m^{2/3}\cdot f_0^2$, of the fruit, and a step for determining the texture and the ripeness of the fruit from the relation between the viscosity value c and the elasticity value E.

Also, an apparatus for measuring the ripeness and the texture of a fruit in the present invention comprises a vibration applying unit for applying a vibration to a fruit to be measured, a second vibration detecting unit for detecting the intensity of a vibration applied to the fruit and generating the signal of the vibration detected, a first vibration detecting unit for detecting the intensity of the vibration of the fruit to which the vibration is applied by the vibration applying unit and generating the signal of the vibration detected, a weight gauge for measuring the weight of the fruit and generating the signal of the weight measured, a secondary resonance point computing unit having functions of finding the transfer functional characteristic of the fruit by performing frequency analysis based on the output signals of the first vibration detecting unit and the second vibration detecting unit, and computing a secondary resonance frequency $f_0$ (i.e., frequency of secondary resonance peak) of the fruit and frequencies f1 and f2 which represent the frequencies of the fruit, at which respective gains are 3 dB lower than the gain at the frequency $f_0$ of the secondary resonance peak, based on the transfer functional characteristic of the fruit, and, functions for computing the damping ratio $\eta$, the elasticity value E and the viscosity value c of the fruit from the output signal of the weight gauge and the frequencies $f_0$, f1 and f2, outputting the signals of the results computed, and also displaying the output signals of the results.

In the present invention, the elasticity value E, the damping ratio $\eta$ and the viscosity value c of the fruit are computed based on the weight and the secondary resonance peak of the fruit to which a vibration is applied, and the ripeness and the texture of the fruit are determined by using these three values which represent the characteristics of the fruit. The above method and apparatus of the present invention enable accurate and high speed judgment of the suitable time for eating of the fruit without damaging the fruit, which also enables timely shipment of foodstuff such as a tomato, a kiwifruit, an apple, a melon and the like to the market.

DESCRIPTION OF THE PREFERRED EMBODIMENTS

Hereinafter a first exemplary embodiment of the present invention is described referring to FIG. 1 through FIG. 4.

Figure 1:
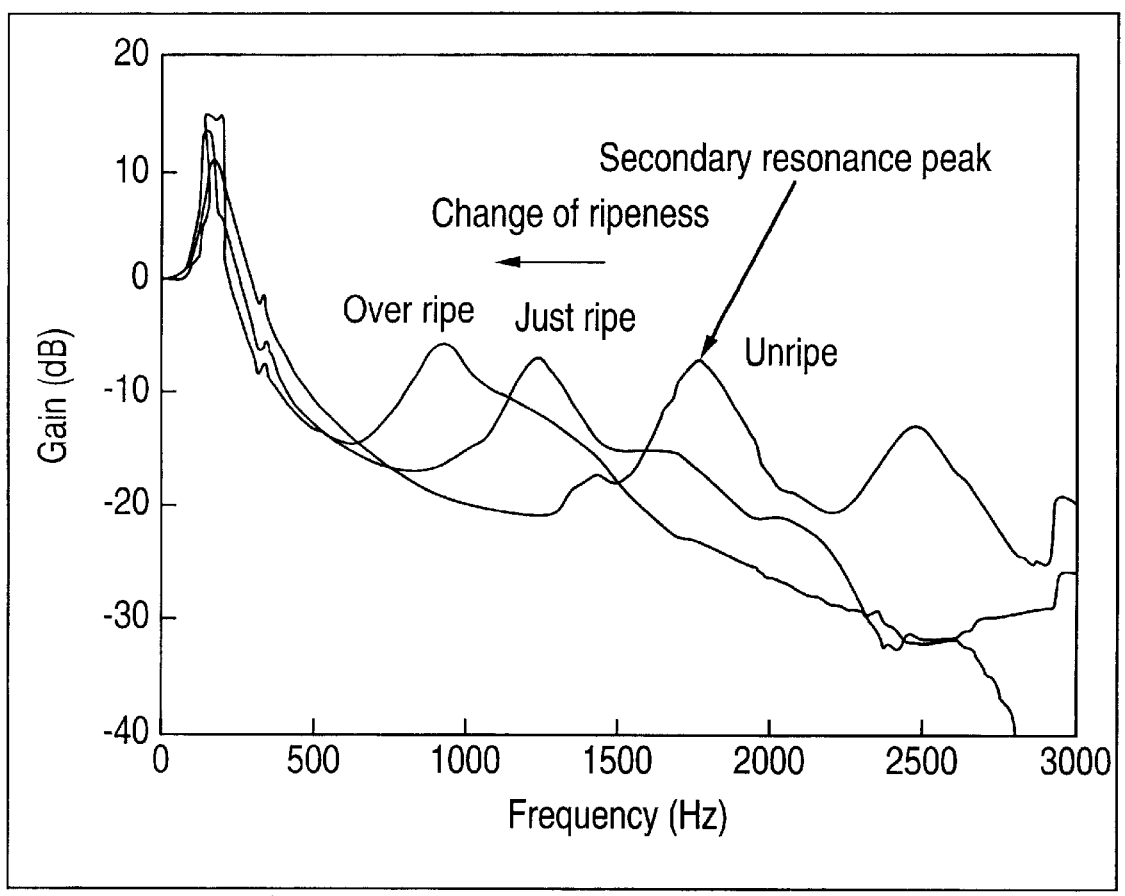
FIG. 1 shows a shift of a secondary resonance peak by ripening in a kiwifruit.

FIG. 1 shows a shift of a secondary resonance peak by ripening in a kiwifruit. As shown in FIG. 1, the frequency at the secondary resonance peak (i.e., secondary resonance frequency) shifts toward the low frequency side according to the change of the ripeness from unripe to over ripe.

Figure 2:
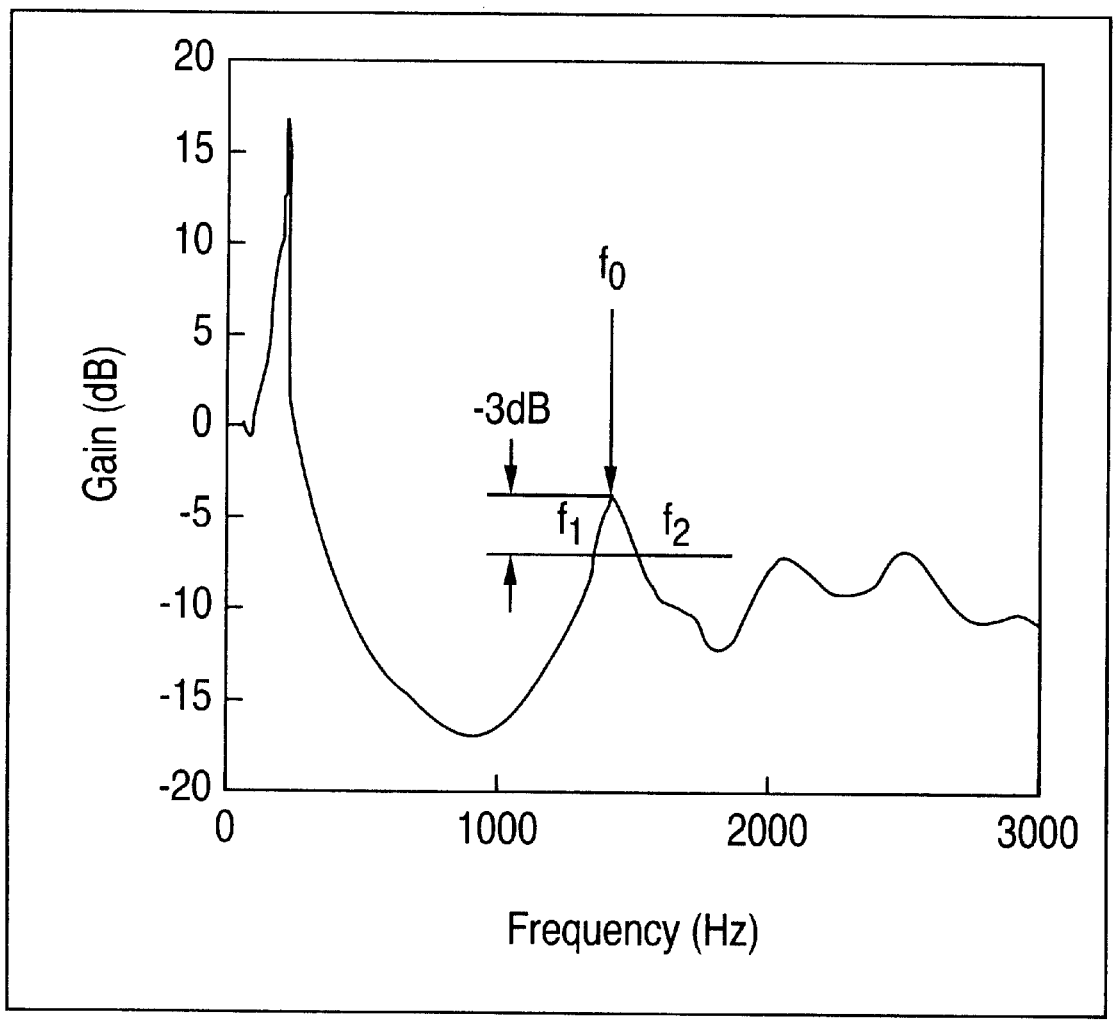
FIG. 2 shows a transfer functional characteristic of a fruit having a secondary resonance peak from which a damping ratio of the fruit is computed.

FIG. 2 shows a transfer functional characteristic of a fruit having a secondary resonance peak from which a damping ratio of the fruit is computed. The damping ratio $\eta$ is computed by the following equation:

In the equation, f1 and f2 represent the frequencies of the fruit at which the respective gains are 3 dB lower than the gain at the frequency $f_0$ of the secondary resonance peak.

The elasticity value E of the fruit can be computed by the following theoretical equation proposed by Cooke:

$$E = m^{2/3} \cdot f_0^2$$

In the equation, m represents the weight of the fruit.

The viscosity value c of the fruit is computed by the following equation:

$$c = 2\pi \cdot f_0 \cdot m \cdot \eta$$

Figure 3:
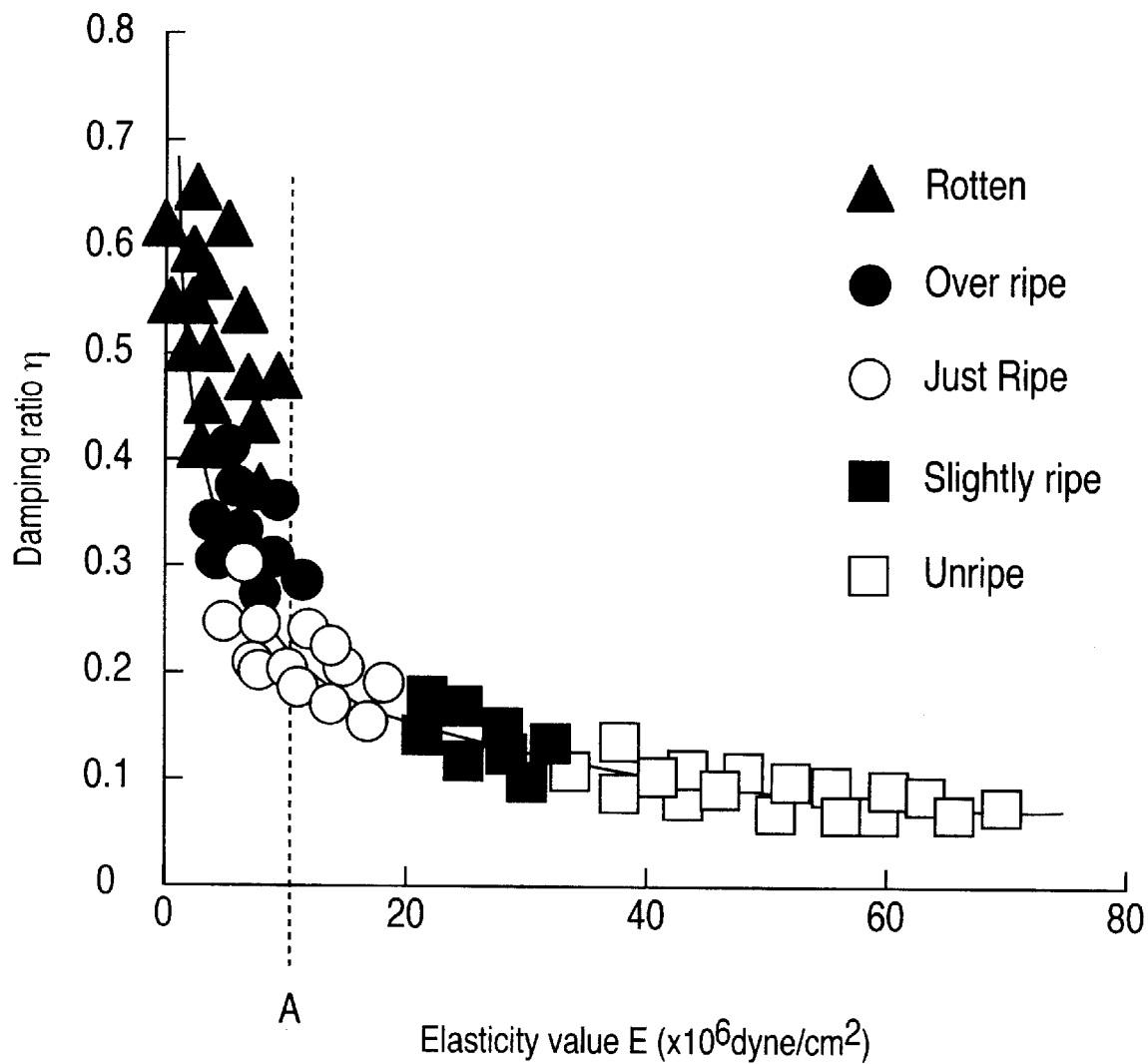
FIG. 3 shows the relation between damping ratios and elasticity values in kiwifruits of various ripeness.

FIG. 3 shows the relation between the damping ratios $\eta$ and the elasticity values E in the kiwifruits of various ripeness.

As shown in FIG. 3, when the elasticity value E is larger than A (e.g. $10 \times 10^6$ dyne/cm$^2$), the ripeness of the kiwifruit successively changes from "just ripe" to "slightly ripe" and to "unripe" according to the increase of the elasticity value E. However, on the line where the elasticity value E is A, just ripe, over ripe and rotten kiwifruits exist. Therefore, the ripeness of the kiwifruit cannot be discriminated by the elasticity value E when the elasticity value E is A or not larger than A. In that case, the discrimination of the ripeness of the kiwifruits is performed by using the damping ratio $\eta$ because the ripeness of the kiwifruits changes from "just ripe" to "over ripe" and to "rotten" according to the increase of the damping ratio $\eta$ as shown in FIG. 3. As described above, by using the elasticity value E when the elasticity value E is larger than A, and the damping ratio $\eta$ when the elasticity value is not larger that A, wide range of discrimination (i.e., from unripe to rotten) can be performed.

The value of A is $10 \times 10^6$ dyne/cm$^2$ in a kiwifruit. However, since the value is different depending on the kind of fruit, the values have to be determined in advance by measuring many samples of each kind of fruit. Also, since the damping ratios $\eta$ and the elasticity values E of a fruit for discriminating the ripeness of the fruit are different for each kind of fruit, these ratios and values have to be determined in advance for each kind of fruit.

Figure 4:
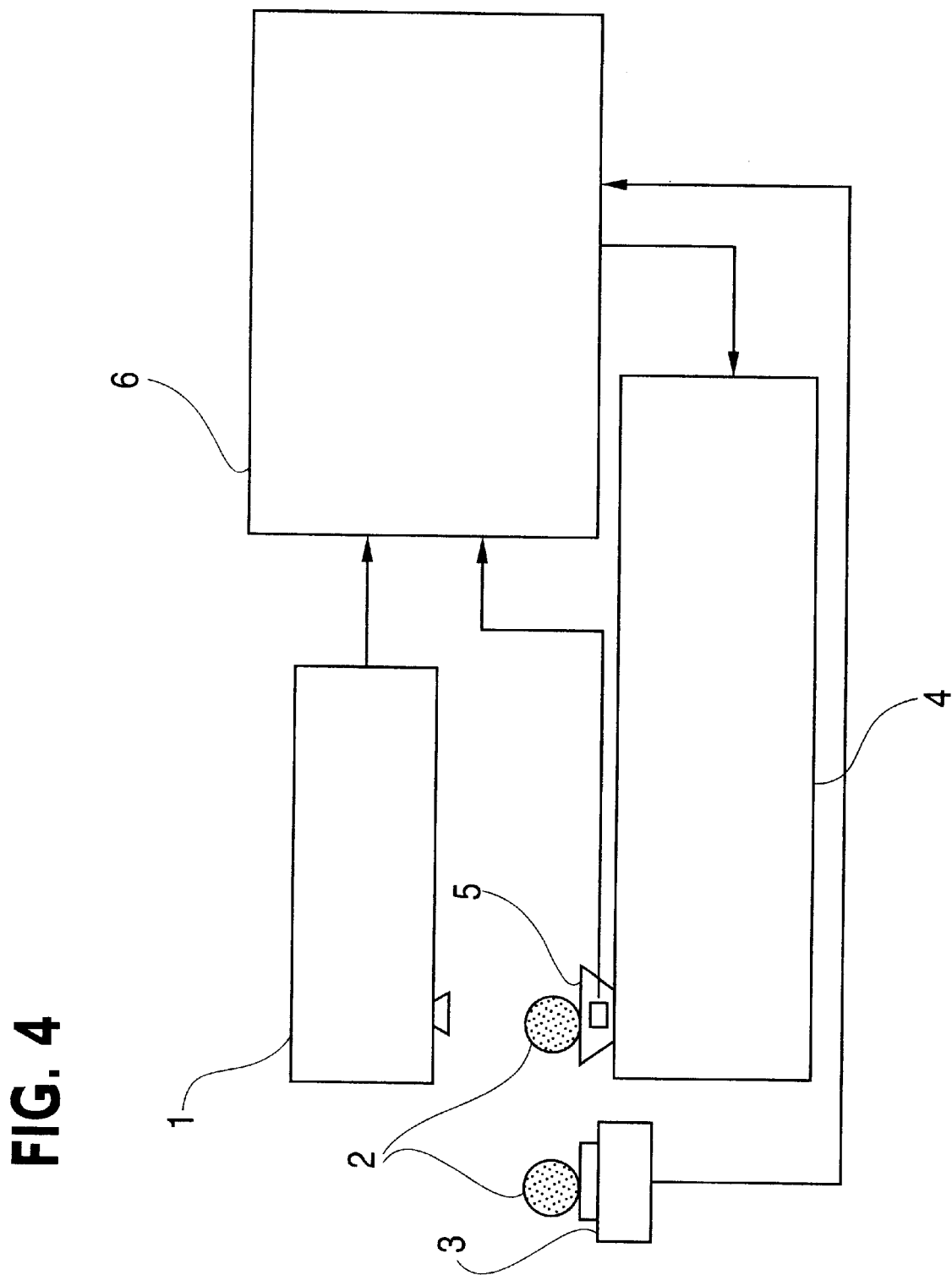
FIG. 4 is a block diagram showing the structure of an apparatus for measuring the ripeness and the texture of a fruit in a first exemplary embodiment of the present invention.

FIG. 4 is a block diagram showing the structure of an apparatus for measuring the ripeness and the texture of a fruit in the first exemplary embodiment of the present invention.

In FIG. 4, a first vibration detecting unit 1 detects the intensity of the vibration of the surface of a fruit 2 to be measured without touching the fruit 2 and converts the vibration to an electric signal, a weight gauge 3 measures the weight of the fruit 2 and generates a signal representing the weight measured, a vibration applying unit 4 applies a predetermined vibration to the fruit 2, a second vibration detecting unit 5 detects the intensity of a vibration applied to the fruit 2 and generates a signal representing the vibration detected, a secondary resonance point computing unit 6 has functions for finding the transfer functional characteristic of the fruit 2 by performing frequency analysis based on the output signals of the first vibration detecting unit 1 and the second vibration detecting unit 5, and computing the secondary resonance frequency $f_0$ (i.e., frequency of secondary resonance peak) of the fruit 2 and frequencies f1 and f2 which represent the frequencies of the fruit 2, at which respective gains are 3 dB lower than the gain at the frequency $f_0$ of the secondary resonance peak, based on the transfer functional characteristic of the fruit 2, and, functions for computing the damping ratio η, the elasticity value E and the viscosity value c of the fruit 2 based on the output signal of the weight gauge 3 and the frequencies $f_0$, f1 and f2, and, outputting the signals of the results computed, also displaying the output signals of the results.

The process for measuring the ripeness and the texture of the fruit 2 by the apparatus having the above structure is described hereinafter.

The fruit 2 is placed on the weight gauge 3 and the signal of the weight m measured is fed into the secondary resonance point computing unit 6. After that, the vibration applying unit 4 sequentially applies, to the fruit 2, a vibration having frequencies of predetermined intervals ranging from a first frequency (e.g., 20 Hz) to a second frequency (e.g., 3 KHz). In this case, the vibration applying unit 4 is driven based on a signal generated by the secondary resonance point computing unit 6. The vibration applied to the fruit 2 is detected by the second vibration detecting unit 5, and the signal of the vibration detected is fed into the secondary resonance point computing unit 6.

On the other hand, the vibration of the fruit 2 to which the vibration is applied is detected by the first vibration detecting unit 1, and the signal of the vibration detected is fed into the secondary resonance point computing unit 6. Then the secondary resonance point computing unit 6 performs frequency analysis by operating a frequency response function based on the signal of the vibration which is obtained through the vibration detecting units 1 and 5 by applying, to the fruit 2, a vibration having frequencies of predetermined intervals ranging from the first frequency to the second frequency, and thereby finds the transfer functional characteristic of the fruit 2 as shown in FIG. 2. Then, the secondary resonance point computing unit 6 computes the damping ratio η, the elasticity value E and the viscosity value c of the fruit 2 based on the output signal of the weight gauge and the resonance frequencies $f_0$, f1 and f2 which are computed from the transfer functional characteristic of the fruit 2, then outputs the signals of the results computed and displays the output signals of the results.

Figure 5:
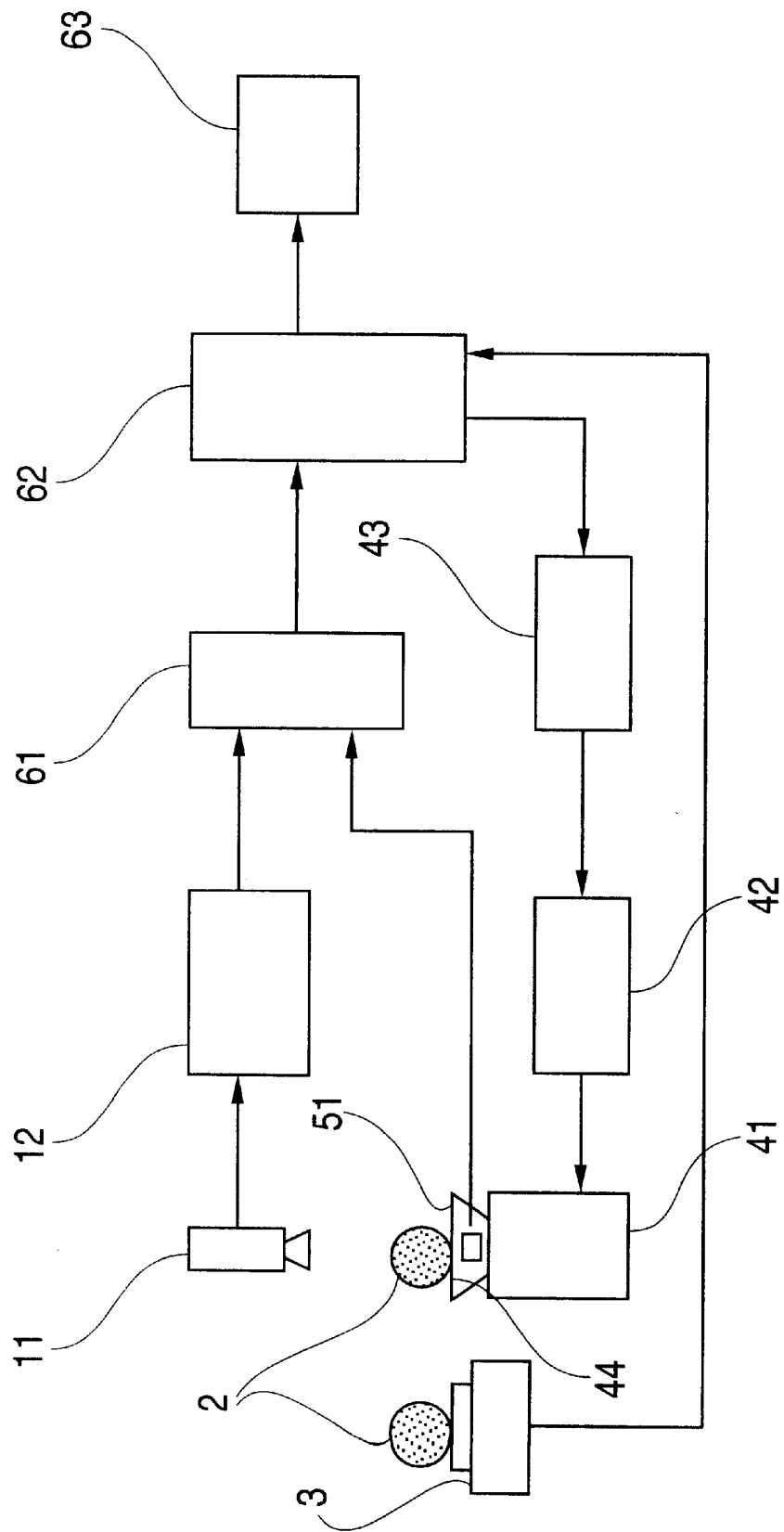
FIG. 5 is a block diagram showing the structure of an apparatus for measuring the ripeness and the texture in a second exemplary embodiment of the present invention.

FIG. 5 is a block diagram showing the structure of an apparatus for measuring the ripeness and the texture of a fruit in a second exemplary embodiment of the present invention.

In FIG. 5, for the elements which are common to the first exemplary embodiment, the same reference numerals are applied and the description on these are omitted. In the second exemplary embodiment, the apparatus comprises a microprocessor for realizing the computing function of the secondary resonance point computing unit 6.

In FIG. 5, a laser Doppler vibration gauge 11 detects the vibration of the surface of the fruit 2 to be measured without touching the fruit 2 and generates a beat signal which changes in proportion to the speed of the fruit 2, a demodulator 12 converts the beat signal generated by the laser Doppler vibration gauge 11 to a vibration signal, a vibration generator 41 is mechanically connected to a rack 44 on which the fruit 2 is placed and applies a predetermined vibration to the fruit 2 through the rack 44, an electric power amplifier 42 generates a signal, which is fed into the vibration generator 41, for generating the vibration applied to the fruit 2, a signal generator 43 generates a signal, which is fed into the electric power amplifier 42, for generating the vibration applied to the fruit 2, an acceleration sensor 51 set in the rack 44 detects the vibration applied to the fruit 2, and a fast Fourier transform device (hereinafter referred to as FFT) 61 performs fast Fourier transform of the output signals fed from the demodulator 12 and the acceleration sensor 51 respectively, and outputs the signals thus transformed to a microprocessor 62. The microprocessor 62 has functions for computing the damping ratio η, the elasticity value E and the viscosity value c of the fruit 2 based on the output signals of the weight gauge 3 and the FFT 61, and outputs the signals computed, and, a function for generating an electric signal for the vibration applied to the fruit 2, and a display device 63 displays the signals of the results measured, which the microprocessor 62 outputs. a predetermined vibration to the fruit 2 through the rack 44, an electric power amplifier 42 generates a signal, which is fed into the vibration generator 41, for generating the vibration applied to the fruit 2, a signal generator 43 generates a signal, which is fed into the electric power amplifier 42, for generating the vibration applied to the fruit 2, an acceleration sensor 51 set in the rack 44 detects the vibration applied to the fruit 2, a fast Fourier transform device (hereinafter referred to as FFT) 61 performs fast Fourier transform of the output signals fed from the demodulator 12 and the acceleration sensor 51 respectively, and outputs the signals thus transformed to a microprocessor 62, the microprocessor 62 has functions for computing the damping ratio η, the elasticity value E and the viscosity value c of the fruit 2 based on the output signals of the weight gauge 3 and the FFT 61, and outputs the signals computed, and, a function for generating an electric signal for the vibration applied to the fruit 2, a display device 63 displays the signals of the results measured, which the microprocessor 62 outputs.

The process for measuring the ripeness and the texture of the fruit 2 by the apparatus having the above structure is described hereinafter.

The fruit 2 is placed on the weight gauge 3 and the signal of the weight m is fed into the microprocessor 62. After that, the fruit 2 is moved onto the rack 44. Then the microprocessor 62 instructs the signal generator 43 to generate the sign wave of a first frequency (e.g. 20 Hz), which is fed into the vibration generator 41 through the electric power amplifier 42, by which the fruit 2 placed on the rack 44 is vibrated. At this time, the vibration of the rack 44 is detected by the acceleration sensor 51 and the signal represent the vibration detected is fed into the microprocessor 62 through the FFT 61. At the same time, the vibration of the surface of the fruit 2 is detected by the laser Doppler vibration gauge 11 and the signal of the vibration detected is fed into the microprocessor 62 through the demodulator 12 and the FFT 61.

Then the microprocessor 62 operates a frequency response function based on the input signals fed from the FFT 61 on respective sign waves of predetermined interval frequencies ranging from the first frequency to a second frequency (e.g. 3 KHz) which is higher than the first frequency. In this case, the sign waves are generated by the signal generator 43 according to the instruction of the microprocessor 62. As a result, the microprocessor 62 finds the transfer functional characteristic of the fruit 2 as shown in FIG. 2.

In this exemplary embodiment, a sign wave is used as a signal for applying a vibration to the fruit 2. However, the same effect is obtained by using a random wave or a swept sign wave as a signal for applying a vibration to the fruit 2.

Then, the microprocessor 62 computes the ripeness and the texture of the fruit 2 based on the above transfer functional characteristic of the fruit.

Figure 6:
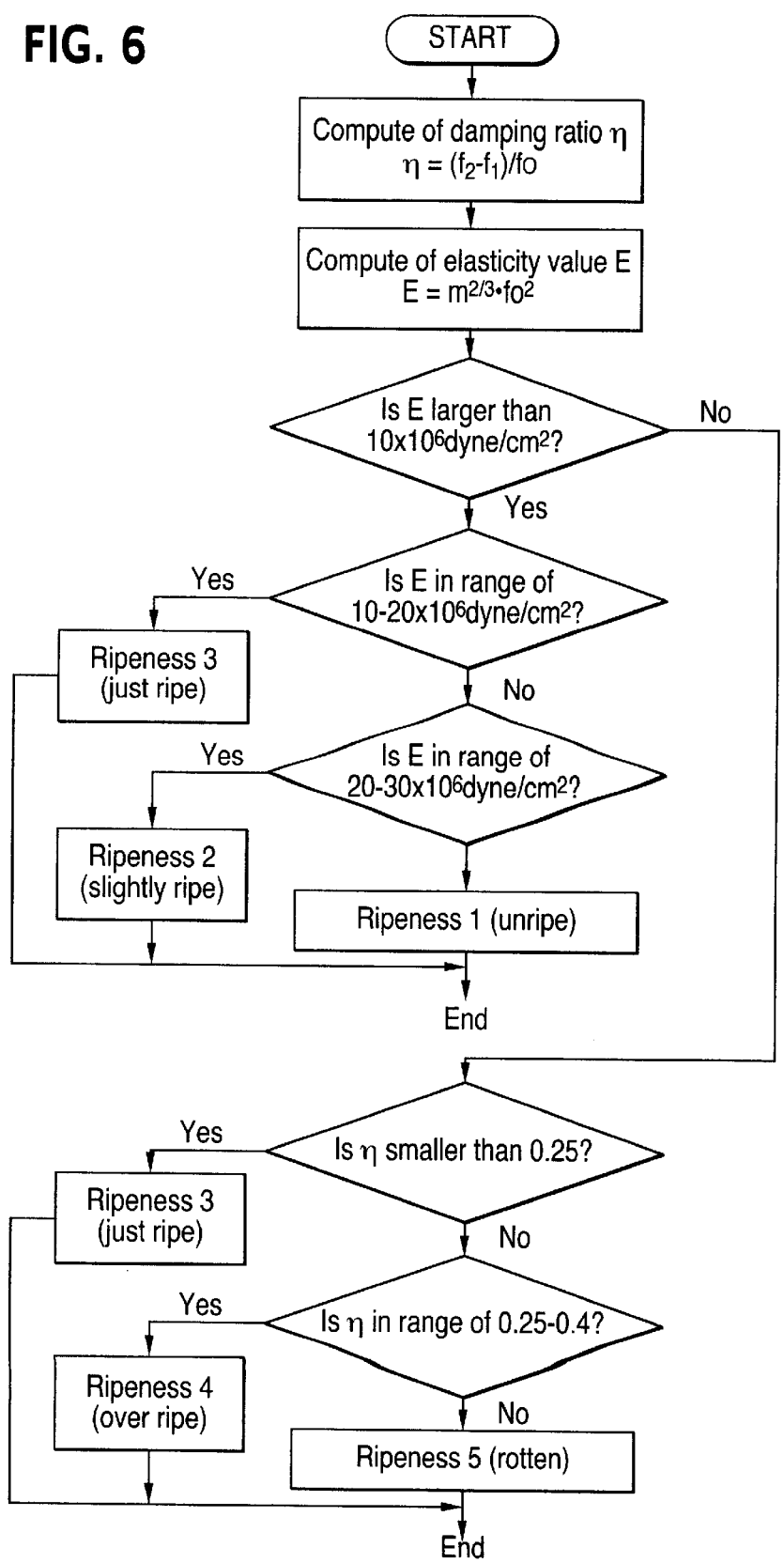
FIG. 6 is a flow chart showing an example of a process for judging the ripeness of a fruit by a microprocessor in the apparatus for measuring the ripeness and the texture of a fruit in the second exemplary embodiment of the present invention.

First, the process for the judgment of the ripeness of the fruit 2 by the microprocessor 62 is described referring to FIG. 6 which is a flow chart showing the process for judging the ripeness of the fruit 2 by the microprocessor 62, in the case of a kiwifruit.

In FIG. 6, the microprocessor 62 computes the elasticity value E of the fruit 2 by the equation $E = m^{2/3} \cdot f_0^2$, in which m represents the weight of the fruit 2 and $f_0$ represents the secondary resonance frequency (i.e., frequency of secondary resonance peak) computed from the transfer functional characteristic of the fruit 2. At the same time, the microprocessor 62 computes the damping ratio $\eta$ of the fruit 2 by the equation $\eta = (f2 - f1)/f_0$, in which f2 and f1 (f2>f1) represent the frequencies of the fruit 2, at which respective gains are 3 dB lower than the gain at the frequency $f_0$ of the secondary resonance peak. Then, the judgment of the ripeness of the fruit is performed by the microprocessor 62 as follows. That is, in the range where the elasticity value E is larger than $10 \times 10^6$ dine/cm$^2$, if the elasticity value E is in the range of $10–20 \times 10^6$ dine/cm$^2$, the ripeness of the fruit is judged to be "3" (just ripe); if the elasticity value E is in the range of $20 –30 \times 10^6$ dine/cm$^2$, the ripeness is judged to be "2" (slightly ripe); and if the elasticity value E is larger than $30 \times 10^6$ dine/cm$^2$, the ripeness is judged to be "1" (unripe). In the range where the elasticity value E is not larger than $10 \times 10^6$ dine/cm$^2$, if the damping ratio $\eta$ is smaller than 0.25, the ripeness is judged to be "3" (just ripe); if the damping ratio $\eta$ is in the range of 0.25–0.4, the ripeness is judged to be "4" (over ripe); and if the damping ratio $\eta$ is larger than 0.4, the ripeness is judged to be "5" (rotten). Then the ripeness of the fruit 2 thus measured is displayed on the display device 63. (unripe). In the range where the elasticity value E is not larger than $10 \times 10^6$ dine/cm$^2$, if the damping ratio $\eta$ is smaller than 0.25, the ripeness is judged to be "3" (just ripe), and, if the damping ratio $\eta$ is in the range of 0.25–0.4, the ripeness is judged to be "4" (over ripe), then, if the damping ratio $\eta$ is larger than 0.4, the ripeness is judged to be "5" (rotten). Then the ripeness of the fruit 2 thus measured is displayed on the display device 63.

Next, for finding the texture of the fruit 2, the viscosity value and the elasticity value for showing the texture of the fruit 2 can be computed by the microprocessor 62 in the same manner as in computing the elasticity value and the damping ratio for judging the ripeness, by using the equations described in the above first and second exemplary embodiments and the transfer functional characteristic of the fruit of FIG. 2.

Figure 7:
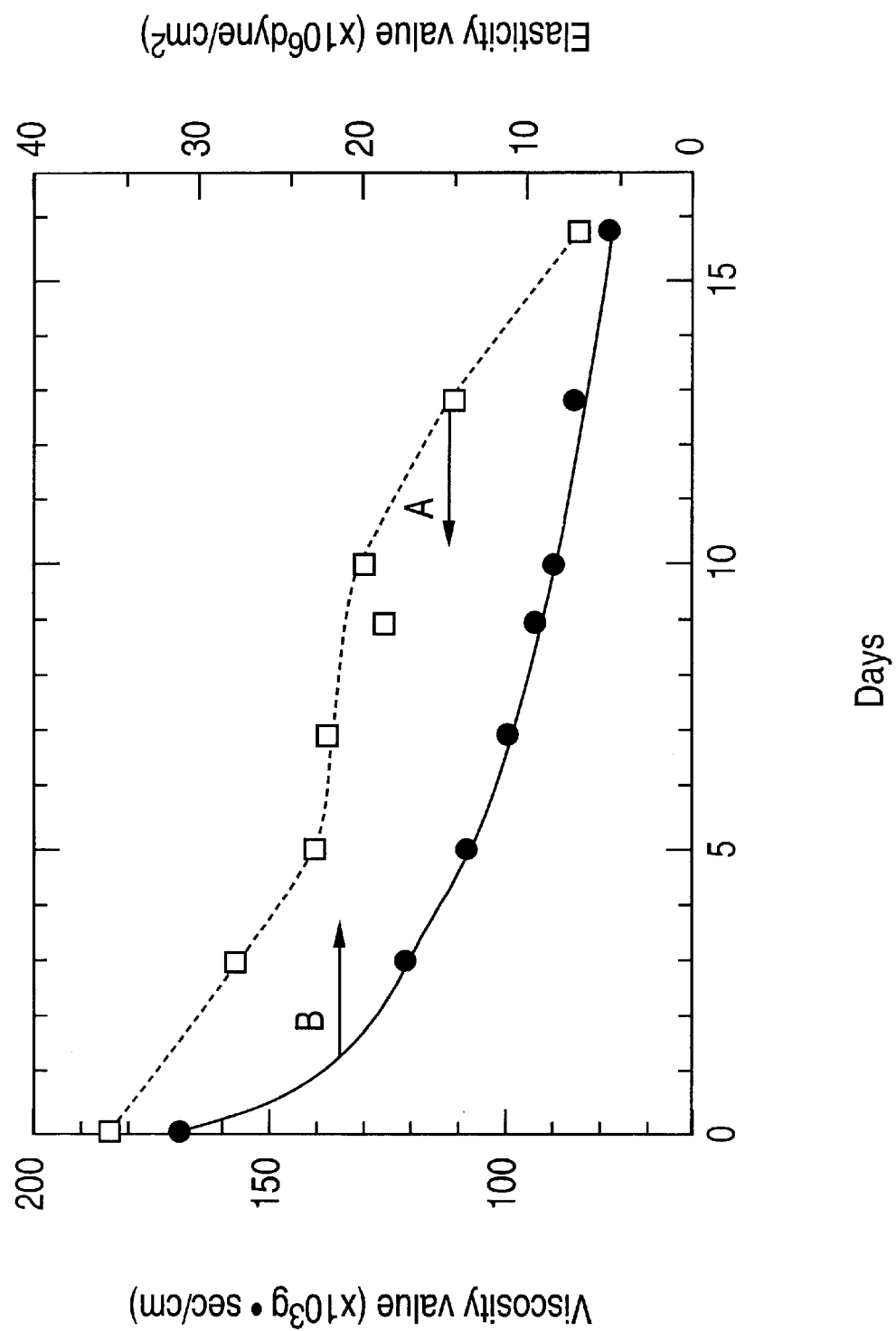
FIG. 7 shows daily change of a viscosity value and an elasticity value of a kiwifruit in measurements performed by the apparatus for measuring the ripeness and the texture of a fruit in the second exemplary embodiment of the present invention.
Figure 8:
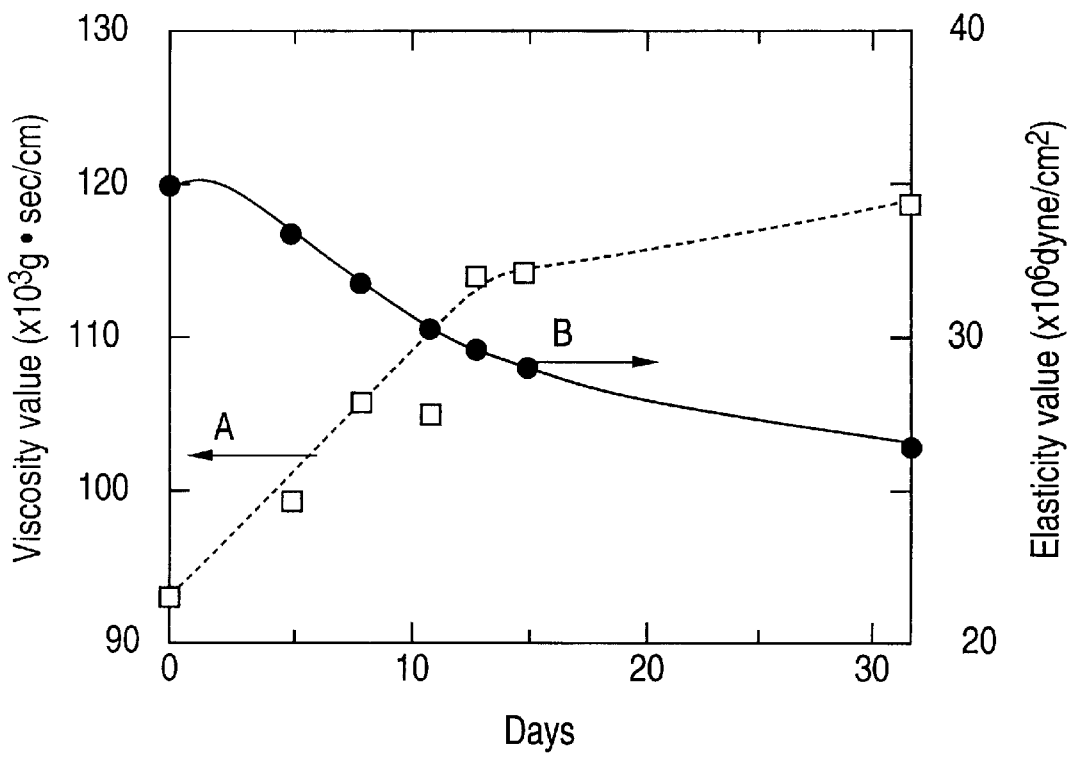
FIG. 8 shows daily change of a viscosity value and an elasticity value of an apple in measurements performed by the apparatus for measuring the ripeness and the texture of a fruit in the second exemplary embodiment of the present invention.
Figure 9:
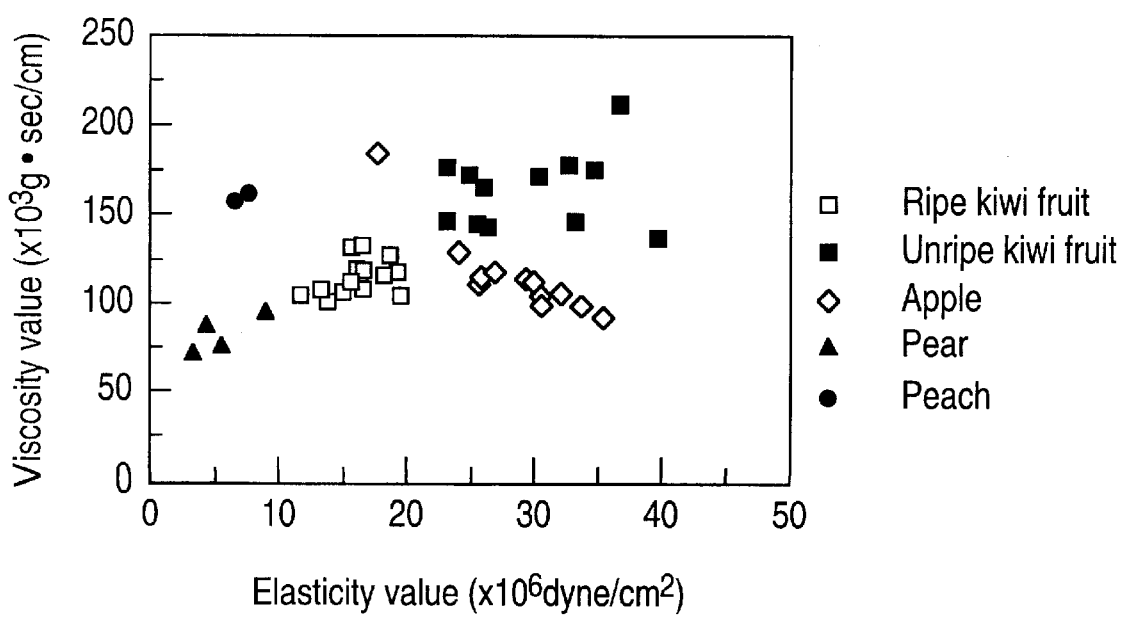
FIG. 9 shows the relation between viscosity values and elasticity values in various fruits in measurements performed by the apparatus for measuring the ripeness and the texture of a fruit in the second exemplary embodiment of the present invention.

FIG. 7 through FIG. 9 show the viscosity values and the elasticity values of various fruits from measurements performed by the apparatus for measuring the ripeness and the texture of a fruit in the second exemplary embodiment of the present invention.

FIG. 7 shows daily change of the viscosity value and the elasticity value of a kiwifruit in measurements performed by the apparatus in the second exemplary embodiment of the present invention. In FIG. 7, the axis of abscissas represents days (i.e., time) and the axis of ordinates represents the viscosity value and the elasticity value of the kiwifruit. The data shown by an arrow A are those of viscosity values, and the data shown by an arrow B are those of elasticity values. As shown in FIG. 7, both the viscosity value and the elasticity value decrease daily. In other words, the flesh of the kiwifruit becomes soft and the juiciness increases daily, and rots to pulp on and after 13th days. The decrease of the elasticity value means that the flesh of the kiwifruit becomes soft, and the decrease of the viscosity value means that the juiciness increases (i.e., decrease of glutinousness).

FIG. 8 shows the daily change of the viscosity value and the elasticity value of an apple in measurements performed by the apparatus in the second exemplary embodiment of the present invention. The axis of abscissas represents days (time) and the axis of ordinates represents the viscosity value and the elasticity value of the apple. The data shown by an arrow A are those of viscosity values, and the data shown by an arrow B are those of elasticity values. As shown in FIG. 8, the viscosity value increases and the elasticity value decreases daily. That is, in the apple, different from the kiwifruit, the juiciness of the flesh decreases and the flesh becomes drier though the flesh becomes softer day by day. In other words, in the apple, the viscosity value of the flesh increases because the juiciness of the flesh decreases and the flesh becomes dry, though the elasticity value decreases as in the case of the kiwifruit of FIG. 7.

FIG. 9 shows the relations between viscosity values and elasticity values in various kinds of fruits (i.e., unripe kiwifruits, ripe kiwifruits, pears, apples and peaches). The data are obtained by measurements performed by the apparatus in the second exemplary embodiment of the present invention.

As shown in FIG. 9, both elasticity values and viscosity values of unripe kiwifruits are larger than those of ripe kiwifruits, which means that the unripe kiwifruits have harder fleshes and lower juiciness compared with the ripe kiwifruits. In other words, in the kiwifruits, there is a tendency that the viscosity value decreases when the elasticity value decreases, i.e., the juiciness increases when the flesh becomes soft. In the apples, there is a tendency that the viscosity value increases when the elasticity value decreases, which means that the juiciness decreases when the flesh becomes soft. In the pears, there is a tendency that the viscosity value decreases when the elasticity value decreases as in the case of the kiwifruit, which means that juiciness increases when the flesh becomes soft. In the peaches, the viscosity values are high for the elasticity values compared with the pears, which means that the juice of the peaches is more viscous than that of the pears. As described above, the texture of a fruit can be found by measuring the viscosity value of the fruit. Also, by using both viscosity value and elasticity value of the fruit, more exact texture of the fruit can be shown.

Also, since the texture of a fruit changes according to the ripening of the fruit, the ripeness of the fruit can be judged by measuring the texture of the fruit. For instance, as shown in FIG. 9, unripe kiwifruits and ripe kiwifruits can be discriminated by the border lines of the elasticity value of approximately $22 \times 10^6$ dyne/cm$^2$, and the viscosity value of approximately $140 \times 10^3$ g·sec/cm. As described above, the ripeness of a fruit can be judged in such a manner that the viscosity value and the elasticity value of the fruit are compared with the data which are prepared in advance by measuring the viscosity values and the elasticity values of the samples of the same kind of fruit, whose ripeness is known when taking the data.

As described above, the present invention can provide an apparatus for measuring the ripeness and the texture of various kinds of fruits, which can exactly measure with high speed the ripeness and the texture of each of the fruits without damaging the fruit, by computing the viscosity value and the elasticity value of the flesh of the fruit, based on the transfer functional characteristic, the secondary resonance peak and the weight of the fruit to which a vibration is applied.

Also, since the ripeness and the texture of a fruit can be quantitatively measured by the apparatus of the present invention without depending on a sensuous test and without damaging the fruit, the texture of a new kind of fruit in plant breeding can be quickly and exactly judged, which enables the a decrease in time needed for the improvement of a fruit in the plant breeding.

What is claimed is:

1. A method for measuring ripeness and texture of a fruit, the method comprising:
    a step for applying a vibration having sequentially changing frequencies to a fruit to be measured;
    a step for measuring an intensity of the vibration applied to said fruit and an intensity of the vibration of said fruit;
    a step for measuring the weight of said fruit;
    a step for finding a transfer functional characteristic of said fruit by performing frequency analysis based on the intensity of the vibration applied to said fruit and the intensity of the vibration of said fruit, and computing a secondary resonance frequency $f_0$ of said fruit and frequencies f2 and f1 which represent the frequencies of said fruit, at which respective gains are 3 dB lower than the gain at the secondary resonance frequency $f_0$, based on said transfer functional characteristic of said fruit;
    a step for computing a damping ratio η defined by an equation η=(f2−f1)/$f_0$;
    a step for computing an elasticity value E defined by an equation E=$m^{2/3} \cdot f_0^2$, of said fruit, wherein m represents the weight of said fruit;
    a step for computing a viscosity value c defined by an equation c=k·$f_0$·m·η;
    a step for determining the ripeness of said fruit by using said elasticity value E when said elasticity value E is larger than a predetermined value, and by using said damping ratio η when said elasticity value E is not larger than said predetermined value; and
    a step for determining the texture of said fruit from relation between said viscosity value c and said elasticity value E.

2. An apparatus for measuring ripeness and texture of a fruit, the apparatus comprising:
    (a) vibration applying means for applying a vibration to a fruit to be measured;
    (b) second vibration detecting means for detecting an intensity of the vibration applied to the fruit, and generating a second vibration signal representing the vibration detected;
    (c) first vibration detecting means for detecting an intensity of the vibration of the fruit to which said vibration is applied, and generating a first vibration signal representing the vibration detected;
    (d) a weight gauge for measuring the weight of the fruit, and generating a weight signal representing the weight measured; and
    (e) secondary resonance point computing means having:
        (e-1) functions for finding the transfer functional characteristic of the fruit by performing frequency analysis based on the first and second vibration signals, and computing a secondary resonance frequency $f_0$ and frequencies f1 and f2 which are frequencies of the fruit, at which respective gains are 3 dB lower than the gain at the secondary resonance frequency $f_0$, based on said transfer functional characteristic of the fruit; and
        (e-2) functions for computing a damping ratio η, an elasticity value E and a viscosity value c of the fruit based on the weight signal and said frequencies $f_0$, f1 and f2, outputting signals representing the results computed, and displaying the output signals of said results computed.

3. The apparatus according to claim 2, wherein the elasticity value of the fruit is computed based on the weight and the secondary resonance frequency of the fruit and, the texture of the fruit is measured by using both of said elasticity value and said viscosity value of the same moment.

4. The apparatus according to claim 2, wherein the ripeness of the fruit is measured in such a manner that the elasticity value and the viscosity value of the fruit, which are obtained by measuring the texture of the fruit, are compared with a predetermined elasticity value and a predetermined viscosity value, respectively.

5. An apparatus for measuring ripeness and texture of a fruit, the apparatus comprising:
    a laser Doppler vibration gauge for detecting vibration of the surface of a fruit to be measured without touching the fruit and generating a beat signal which changes in proportion to the speed of the fruit;
    a demodulator for converting said beat signal into a vibration signal;
    a weight gauge for measuring the weight of said fruit and generating a signal representing the weight measured;
    a rack on which the fruit is placed;
    a vibration generator, which is mechanically connected to said rack on which the fruit is placed, for generating a vibration applied to the fruit through said rack;
    an electric power amplifier for generating a signal, which is fed into said vibration generator, for generating said vibration applied to the fruit;
    a signal generator for generating a signal, which is fed into said electric power amplifier, for generating said vibration applied to the fruit;
    an acceleration sensor, which is set in said rack, for detecting the vibration applied to said fruit;
    an FFT for performing fast Fourier transform on the output signals of said demodulator and said acceleration sensor respectively, and generating the signals thus transformed;
    a microprocessor having
        functions for computing a damping ratio η, an elasticity value E and a viscosity value c of the fruit based on the output signals of said weight gauge and said FFT, and generating signals representing the results computed, and
        a function for generating an electric signal based on which said vibration applied to said fruit is generated; and
    a display device for displaying the output signals representing the results computed by said microprocessor.

6. The apparatus according to claim 5, wherein said viscosity value is computed by an equation c=k·$f_0$·m·η, wherein m represents the weight of the fruit, $f_0$ represents a secondary resonance frequency of the fruit, η represents a damping ratio of the secondary resonance frequency of the fruit, and k represents a constant.

7. The apparatus according to claim 6, wherein said constant k is 2π.

8. A method for measuring ripeness and texture of a fruit, the method comprising:
    applying a vibration having sequentially changing frequencies to a fruit to be measured;
    measuring an intensity of the vibration applied to said fruit and an intensity of the vibration of said fruit;

measuring the weight of said fruit;

finding a transfer functional characteristic of said fruit by performing frequency analysis based on the intensity of the vibration applied to said fruit and the intensity of the vibration of said fruit, and computing a secondary resonance frequency $f_0$ of said fruit and frequencies f2 and f1 which represent the frequencies of said fruit, at which respective gains are 3 dB lower than the gain at the secondary resonance frequency $f_0$, based on said transfer functional characteristic of said fruit;

computing a damping ratio $\eta$ defined by an equation $\eta=(f2-f1)/f_0$;

computing an elasticity value E defined by an equation $E=m^{2/3}\cdot f_0^2$, of said fruit, wherein m represents the weight of said fruit;

computing a viscosity value c defined by an equation $c=k\cdot f_0\cdot m\cdot \eta$;

determining the ripeness of said fruit by using said elasticity value E when said elasticity value E is larger than a predetermined value, and by using said damping ratio $\eta$ when said elasticity value E is not larger than said predetermined value; and determining the texture of said fruit from relation between said viscosity value c and said elasticity value E.

9. An apparatus for measuring ripeness and texture of a fruit, the apparatus comprising:
   (a) a vibrator for applying a vibration to a fruit to be measured;
   (b) a second vibration detector for detecting an intensity of the vibration applied to the fruit, and generating a second vibration signal representing the vibration detected;
   (c) a first vibration detector for detecting an intensity of the vibration of the fruit to which said vibration is applied, and generating a first vibration signal representing the vibration detected;
   (d) a weight gauge for measuring the weight of the fruit, and generating a weight signal representing the weight measured; and
   (e) a secondary resonance point computing device having:
      (e-1) functions for finding the transfer functional characteristic of the fruit by performing frequency analysis based on the first and second vibration signals, and computing a secondary resonance frequency $f_0$ and frequencies f1 and f2 which are frequencies of the fruit, at which respective gains are 3 dB lower than the gain at the secondary resonance frequency $f_0$, based on said transfer functional characteristic of the fruit; and
      (e-2) functions for computing a damping ratio $\eta$, an elasticity value E and a viscosity value c of the fruit based on the weight signal and said frequencies $f_0$, f1 and f2, outputting signals representing the results computed, and displaying the output signals of said results computed.

10. The apparatus according to claim 9, wherein the elasticity value of the fruit is computed based on the weight and the secondary resonance frequency of the fruit and, the texture of the fruit is measured by using both of said elasticity value and said viscosity value of the same moment.

11. The apparatus according to claim 9, wherein the ripeness of the fruit is measured in such a manner that the elasticity value and the viscosity value of the fruit, which are obtained by measuring the texture of the fruit, are compared with a predetermined elasticity value and a predetermined viscosity value, respectively.

* * * * *